(12) United States Patent
Nicholls et al.

(10) Patent No.: US 8,388,639 B2
(45) Date of Patent: Mar. 5, 2013

(54) LANCING DEVICES

(75) Inventors: Clive Nicholls, Buckinghamshire (GB); Robert Michael Wozencroft, Epsom (GB)

(73) Assignee: Owen Mumford Limited, Oxford (GB)

( * ) Notice: Subject to any disclaimer, the term of this patent is extended or adjusted under 35 U.S.C. 154(b) by 93 days.

(21) Appl. No.: 12/673,634

(22) PCT Filed: Aug. 14, 2008

(86) PCT No.: PCT/GB2008/002756
§ 371 (c)(1),
(2), (4) Date: Jun. 1, 2010

(87) PCT Pub. No.: WO2009/022144
PCT Pub. Date: Feb. 19, 2009

(65) Prior Publication Data
US 2010/0324582 A1      Dec. 23, 2010

(30) Foreign Application Priority Data
Aug. 14, 2007  (GB) .................................. 0715798.5

(51) Int. Cl.
*A61B 5/151* (2006.01)

(52) U.S. Cl. ........................................ 606/182

(58) Field of Classification Search .......... 606/181–185, 606/117, 167; 604/131, 134; 600/573, 583
See application file for complete search history.

(56) References Cited

U.S. PATENT DOCUMENTS

| | | | |
|---|---|---|---|
| 5,269,799 A | 12/1993 | Daniel | |
| 5,279,294 A | 1/1994 | Anderson et al. | |
| 5,423,847 A | 6/1995 | Strong et al. | |
| 6,197,040 B1 | 3/2001 | LeVaughn et al. | |
| 7,273,484 B2 | 9/2007 | Thoes et al. | |
| 2003/0028126 A1* | 2/2003 | List | 600/583 |
| 2005/0090850 A1 | 4/2005 | Thoes et al. | |
| 2005/0288637 A1* | 12/2005 | Kuhr et al. | 604/204 |
| 2009/0069832 A1 | 3/2009 | Kitamura et al. | |

FOREIGN PATENT DOCUMENTS

| | | |
|---|---|---|
| EP | 0 458 451 | 11/1991 |
| EP | 0 569 124 | 11/1993 |
| EP | 1 031 319 | 8/2000 |
| EP | 1 504 718 | 2/2005 |
| WO | 2007018215 A1 | 2/2007 |

OTHER PUBLICATIONS

International Search Report dated Dec. 4, 2008, from corresponding PCT application.
GB search report, dated Nov. 9, 2007, from corresponding GB application.

* cited by examiner

*Primary Examiner* — Victor Nguyen
*Assistant Examiner* — Rachel S Papeika
(74) *Attorney, Agent, or Firm* — Young & Thompson

(57) ABSTRACT

A lancet device includes a main body in which is located a lancet drive shaft 20 having a lancet holder 22 at its front end. A front housing flap 12 is hinged to the front of the main body portion and opens to allow insertion/withdrawal of a lancet. A multi-function cocking/ejection element 16 is operable both to cock the drive shaft prior to firing and to eject a lancet from the lancet holder after firing. The cock/eject element also unlatches the front flap 12.

13 Claims, 5 Drawing Sheets

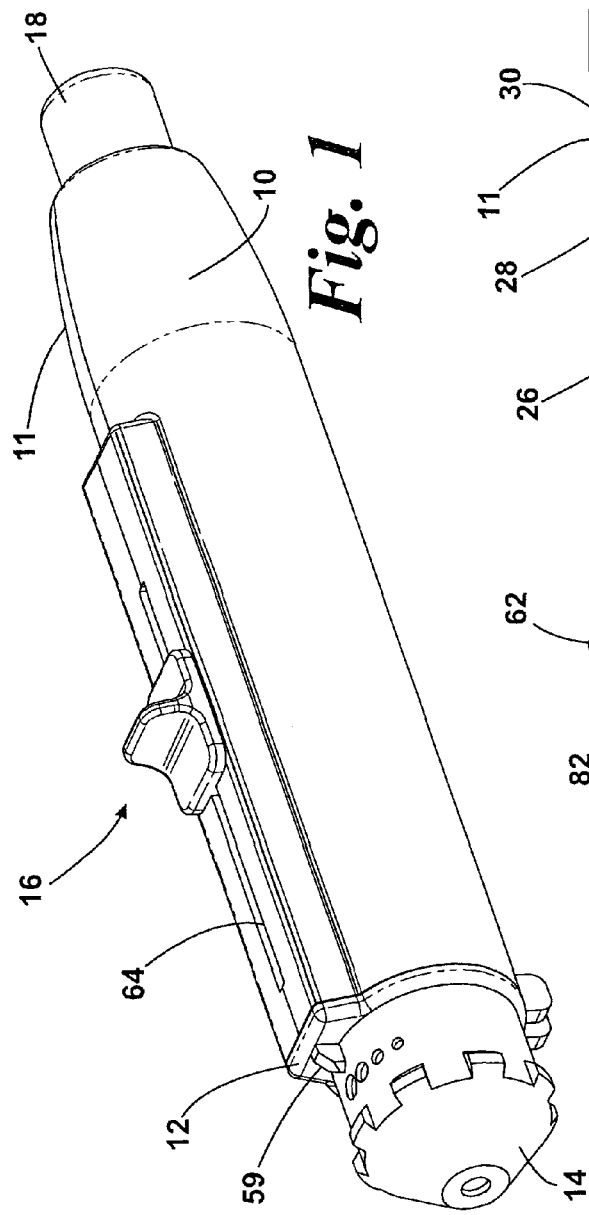
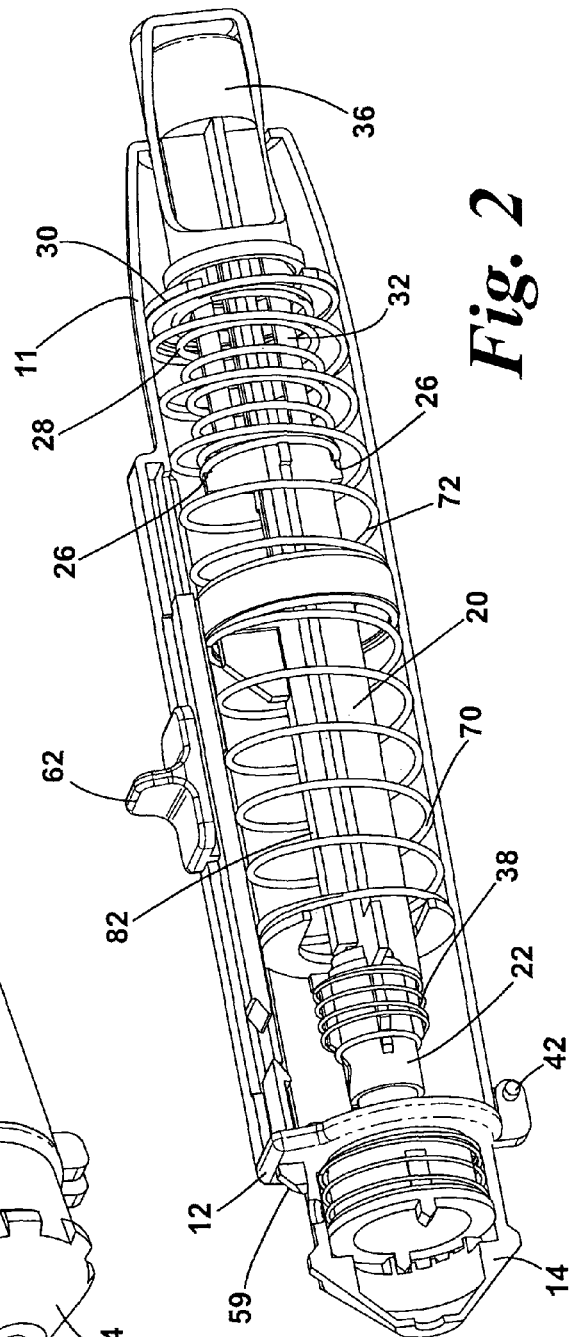

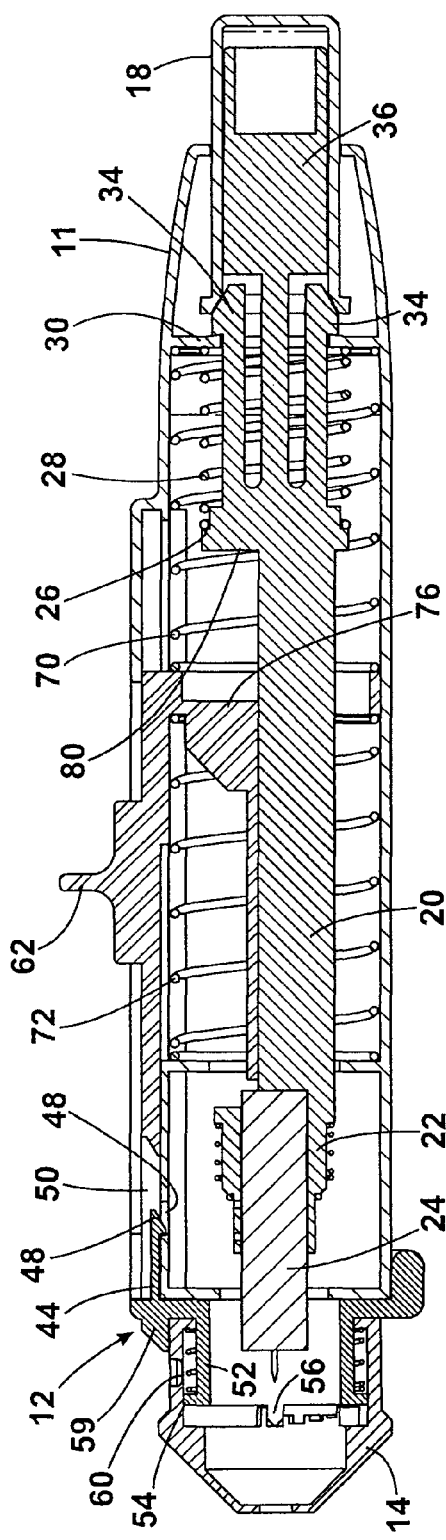

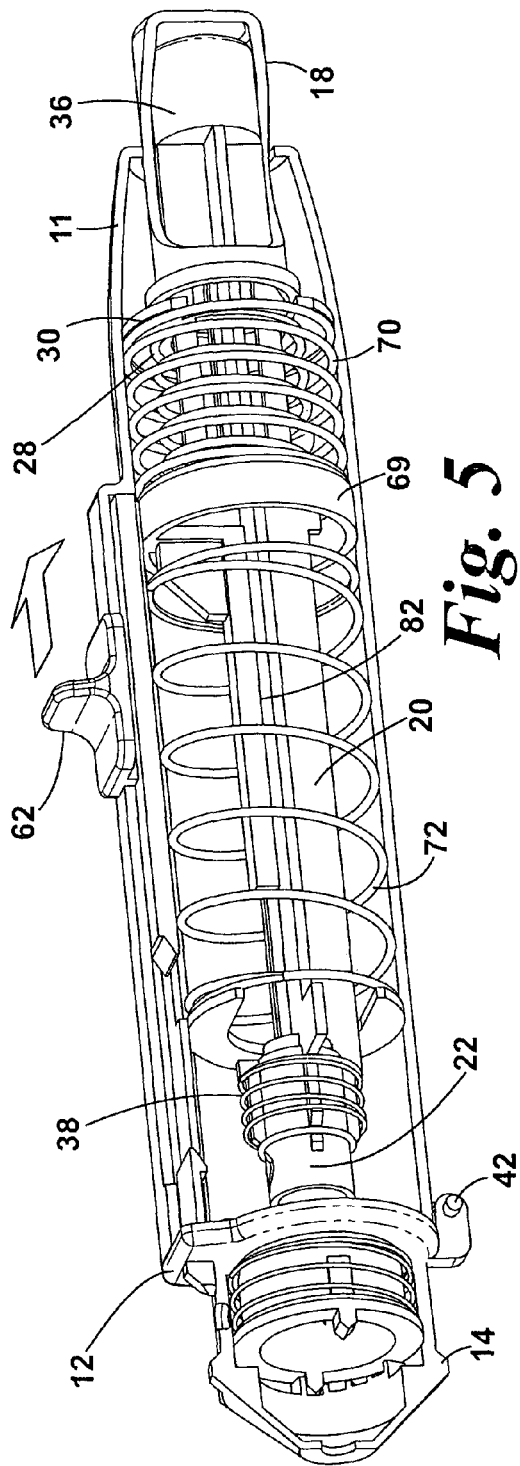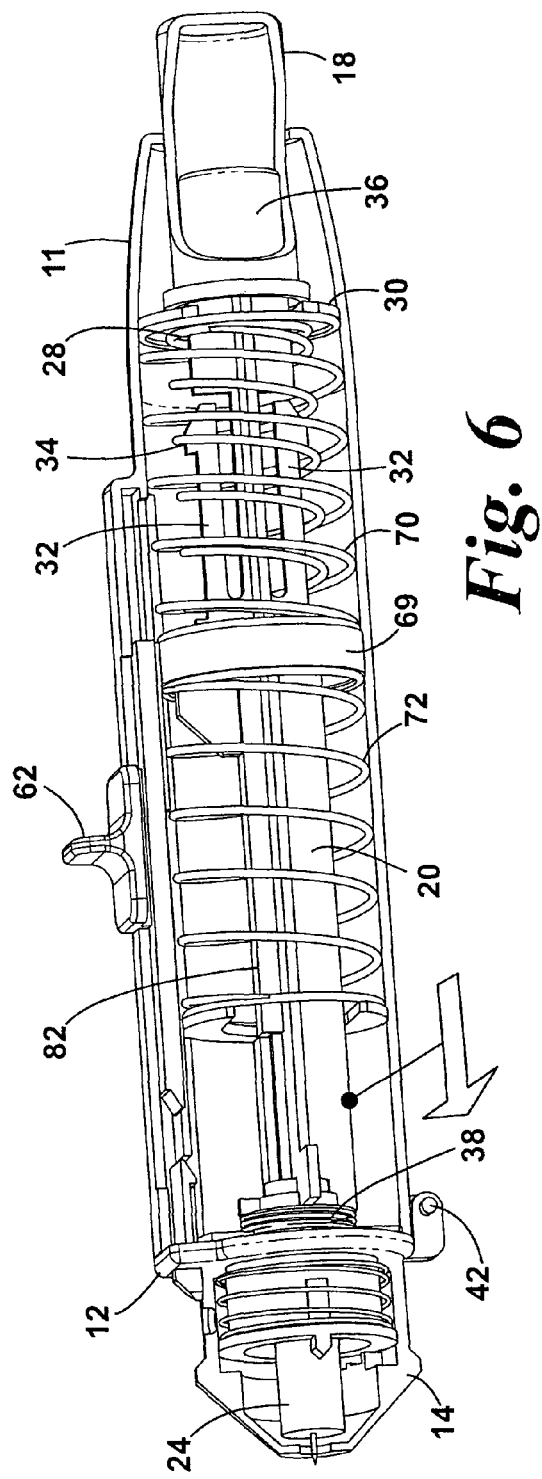

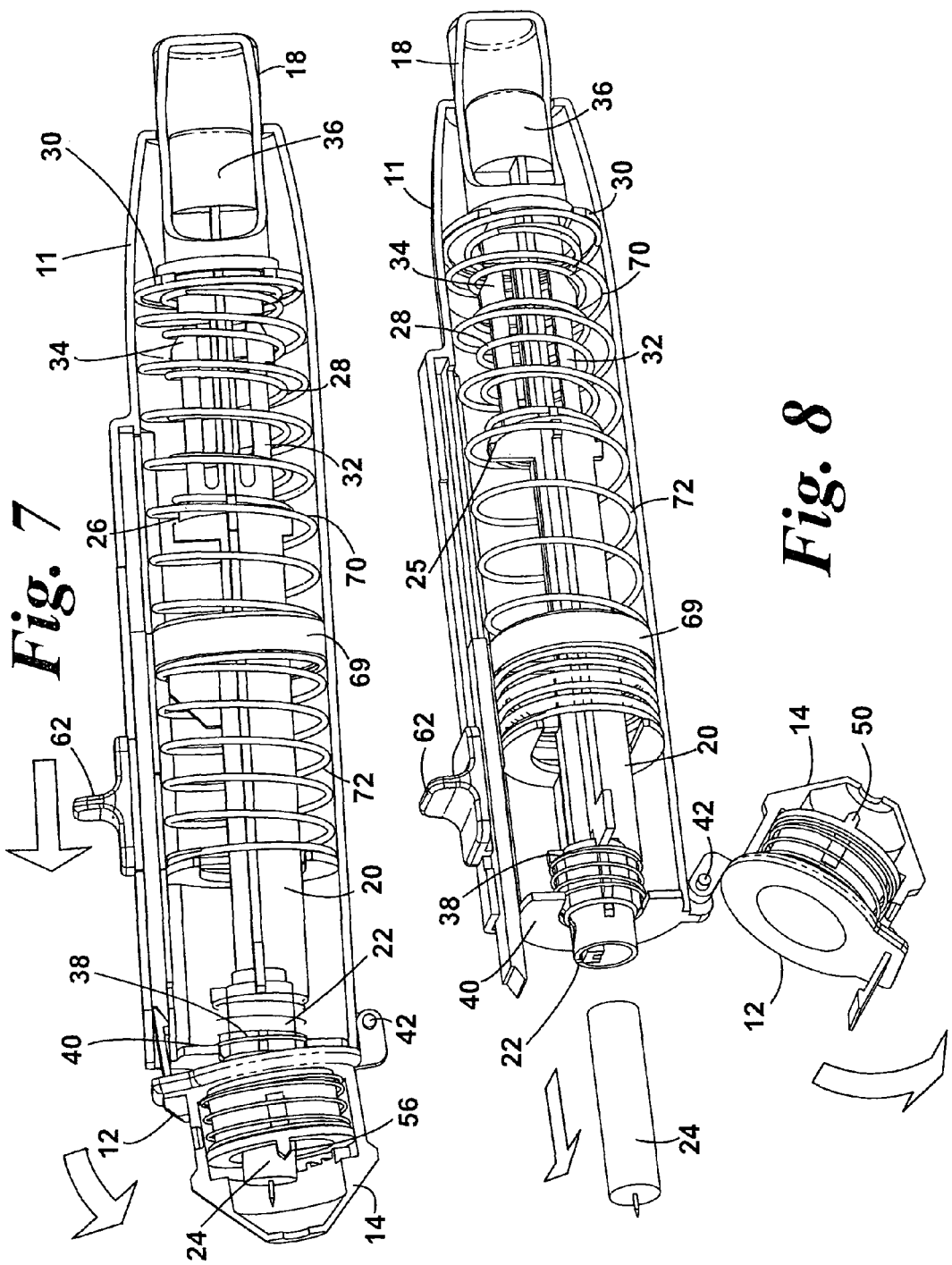

LANCING DEVICES

BACKGROUND OF THE INVENTION

1. Field of the Invention

This invention relates to lancing devices and in particular, but not exclusively, to lancing devices for use with a removable lancet.

2. Description of the Related Art

There are many instances where a user needs to prick the skin to draw a bead of blood for test purposes. To reduce the possibility of cross-infection or contamination, it is known to provide a lancing device with removable or disposable lancets which are removed and disposed after each use. Although a lancing device is reusable for an extended period, it is nevertheless desirable to reduce the component count in order to reduce manufacturing and assembly costs. It is also desirable to reduce the amount of handling of the lancet by the user.

U.S. Pat. No. 5,423,847 discloses a lancet injector which uses two elastomeric bands to drive the lancet forwardly and to rapidly withdraw the lancet from the skin. The injector includes a separate chassis disposed within a housing, a shaft, an ejector and a separate slide member. Movement of the ejector is controlled by engagement with the chassis during various phases of operation of the device. The device is complicated to manufacture and assemble given the number of components. In particular, the injector requires a separate slide member and a chassis in addition to the other components.

SUMMARY OF THE INVENTION

In one aspect, this invention provides a lancing device comprising an outer housing, a drive shaft disposed in the housing for movement between a rearward and a forward position, said drive shaft having a lancet holder means at its forward end for receiving in use a lancet, a drive spring urging said drive shaft in a forward direction, a latch for latching said drive shaft in a rearward cocked position with the drive spring energised, a trigger for unlatching said drive shaft from its rearward position, and a cocking/ejecting element having an externally accessible manually operable portion and being arranged to be moveable in the rearward direction to cock the drive shaft, the cocking/ejecting element further being operable to eject a lancet from the lancet holder.

Although other movements are possible, e.g. rotary, said cocking/ejecting element is preferably moveable forwardly to eject a lancet from said lancet holder.

Said latch preferably includes an abutment provided on the interior of the housing, which cooperates with a corresponding abutment on the drive shaft, one of said abutments being resiliently deflectable out of engagement with the other. For example said shaft or a portion thereof may be resiliently deflectable, and said trigger means may comprise an externally accessible trigger button operable to engage and displace the abutment on said shaft.

The housing may be generally opaque in at least a rearward portion thereof, and said trigger button may comprise a transparent or translucent member having an internal space, with said shaft having an indicator portion on its rearward end which projects into said space when said shaft is in its rearward position, thus indicating the device is cocked.

Said cocking/ejecting element may comprise a spring support portion disposed interiorly of the housing and acted upon by opposing spring means.

Said cocking/ejecting element may have a cocking abutment for engaging said shaft and urging it rearwardly when said cocking/ejecting element is moved rearwardly, and an ejection finger extending forwardly and operable to enter the lancet holder to eject a lancet when said cocking/ejecting element is moved forwardly.

In one arrangement, the outer housing may have a forward portion hingeable with respect to the remainder thereof between an open position in which there is access to said lancet holding means, and a closed position ready for lancing, and said hingeable forward portion may be latchable in said closed position. In this case, said cocking/ejecting element may have an unlatching element disposed to unlatch said hinge portion when said cocking/ejecting element is moved forwardly.

Although the invention has been described above, it extends to any inventive combination or sub-combination of features set out above, or in the following description or claims.

BRIEF DESCRIPTION OF THE DRAWING FIGURES

The invention may be performed in various ways, and an embodiment thereof will now be described by way of example only, reference being made to the accompanying drawings, in which:

FIG. 1 is a general perspective view of a lancing device in accordance with this invention;

FIG. 2 is a perspective view of the lancing device of FIG. 1, when in the cocked position, but with part of the casing removed and other parts cut away for clarity;

FIG. 3 is a longitudinal section view through the lancing device of FIGS. 1 and 2;

FIG. 4 is a top plan view of the lancing device of FIGS. 1 to 3;

FIGS. 5 to 8 are views similar to FIG. 2 but showing the device during various phases of its operation.

DETAILED DESCRIPTION OF THE INVENTION

Figure 9:
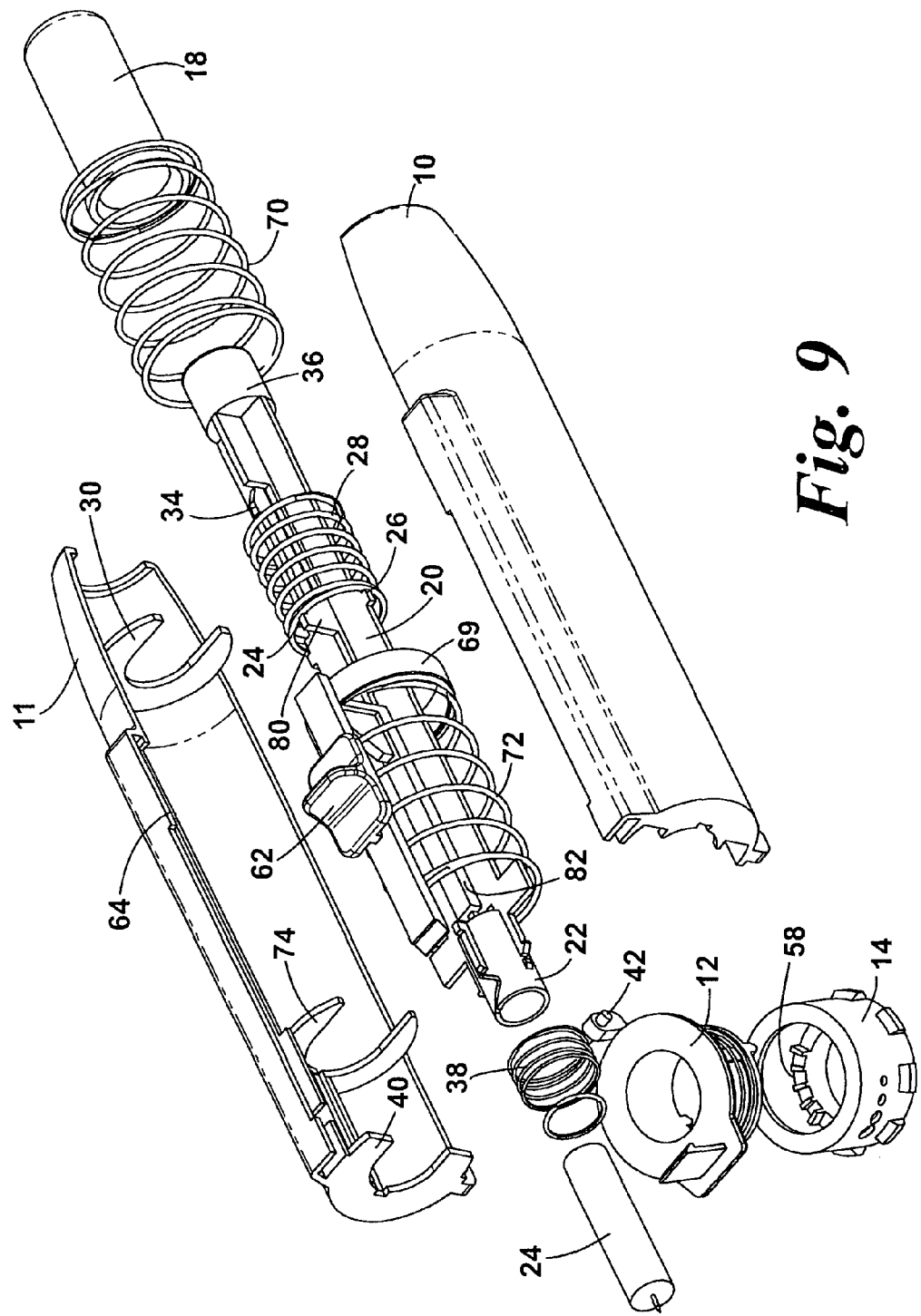
FIG. 9 is an exploded view of the lancing device of FIGS. 1 to 8.

Referring initially to FIG. 1, the illustrated embodiment of lancing device comprises an outer main housing made up of housing halves 10, 11 to the forward end of which is hingedly attached a housing flap 12 on the front of which is mounted a rotary adjustable nose piece 14 for controlling the penetration depth of the lancet. The lancing device is designed to receive a lancet which, on firing, projects its tip through an aperture in the nose piece 14. Cocking of the lancet, unlatching the housing flap 12 and ejection of the lancet from the housing is achieved using a multi-function cocking/ejection element 16. Once cocked, the lancet is fired by pressing a trigger button 18 which projects from the rear of the housing 10.

Referring now more particularly to FIGS. 2 to 9, arranged internally of the housing 10, 11 for longitudinal sliding movement is a lancet drive shaft 20 of generally cruciform cross-section along part of its length. At its forward end there is provided a generally cylindrical lancet holder 22 having an internal space of generally cylindrical form for receiving a lancet 24. The forward half of the drive shaft has the vertical rib of the cruciform cut away to receive the cocking/ejection member 16 as to be described in more detail below. To the rear of the cut away portion the tips of the cruciform members define rearward facing thrust surfaces 26 for the lancet drive spring 28, the opposite end of which engages an internal wall 30 in the housing halves 10, 11. To the rear of the thrust surfaces 26, the upper and lower ribs of the cruciform drive shaft are formed as flexible barbed fingers 32 having heads 34 which, when the drive shaft is urged rearwardly to its cocked position, latch behind the internal wall 30. The shaft continues rearwardly beyond the heads 34 to be formed as an indicator cylinder 36 which, when the lancet drive shaft 20 is cocked, slides into the portion of the trigger button 18 that projects rearwardly from the device to provide an indication that the device is cocked and live. The trigger button 18 is made transparent for this purpose. At the front end of the lancet drive shaft, a coil spring 38 surrounds the lancet holder and is designed to cooperate with a front end wall 40 of the housing half 11 as the shaft shoots forward after driving, to damp the forwardmost movement of the shaft.

The housing flap 12 is held by hinge lugs 42 to the housing halves 10, 11. Whilst not shown, there may be a spring urging the housing flap 12 to the open position and there may be a damper associated with the hinge to damp the opening movement. The housing flap 12 has a rearwardly extending finger 44 with a barbed head 46 that latches in a recess 48 formed in a channel 50 in the housing halves 10, 11. The nose piece 14 is captively mounted on the front end of the housing flap 12 and urged rearwardly by a compression spring 52 acting between an inwardly directed flange on the nose piece 14 and an outwardly directed flange 54 on a cylindrical extension of the nose flap 12. Projecting at diametrically opposed locations on the flange 54 are two forwardly projecting V-head projections 56. These projections cooperate with a series of aligned recesses 58 on an inner wall portion of the nose piece 14. The recesses 58 are of progressively increasing axial extent and the arrangement is such that the nose piece 14 can be pulled forwardly against the bias of the compression spring 52 and then twisted to align the head 56 with the required recess and then released. A pointer 59 on the housing flap 12 cooperates with indicia 60 on the outside of the nose flap to indicate the penetration depth.

The cocking/ejection member 16 has an externally projecting slider 62 which projects through a slot 64. The slider 62 is integrally formed on a longitudinal strip 66 at the forward end of which is an unlatching surface 68 which runs in the slot 50 to cooperate with the barbed head 46 of the housing flap 12. At its rear end, the strip 66 is integral with a spring support ring 69 which is acted upon in the forward direction by a rearward compression spring 70 and in the rearward direction by a forward compression spring 72. At its other end, the rearward compression spring 70 engages the interior wall 30 on the housing 10, 11. At the forward end, the forward compression spring 72 engages an interior wall 74 on the housing half 11.

Extending radially inwardly from the spring support ring 68 there is a cocking rib 76 (see FIG. 3) designed to cooperate with a corresponding cocking rib 80 formed on the shaft 20. Extending from the front surface of the cocking rib 76 is an elongate ejector finger 82 which extends forwardly along the central axis of the shaft 20. The ejector finger 82 is designed to be movable forwardly into the lancet holder 22 from the rear so as to eject a lancet 24 held therein.

In operation, assuming that the device is in the configuration of FIGS. 2 and 3, that is with a lancet 24 loaded in the holder 22 and the shaft 20 in the cocked position with the lancet drive spring compressed and the heads 34 on the shaft latched behind the interior wall 30, the indicator cylinder 36 is projecting into the trigger button 18 to show that the device is armed. The user, having selected the appropriate penetration depth by pulling and twisting the nose piece 14, offers the device up to the skin and then presses the trigger 18. Forward movement of the trigger 18 squeezes the heads 34 towards each other thus releasing the lancet drive shaft 20 so that it shoots forward under the influence of the lancet drive spring 28 to cause the tip of the lancet 24 to project momentarily through the aperture in the nose piece 14, as shown in FIG. 4, as the damping spring 38 on the outside of the lancet holder 22 is compressed against the end wall 40 with the lancet thereafter being urged back into the housing by the action of the spring 38.

The user then slides the cocking/ejection member 16 forwardly so that the release surface 68 on the forward end of the strip 66 disengages the barbed head 46 of the housing flap so that the flap can hinge open, with continued forward movement of the slider 62 causing the ejection finger 82 to eject the lancet 24 from the lancet holder 22, as shown in FIGS. 7 and 8.

For the next operation, the nose flap may be opened if necessary by pushing the slider 62 forward, a lancet 24 may be loaded into the holder 22 and the housing flap 12 snapped shut. The drive shaft is then cocked by sliding the slider 62 rearwardly until the heads 34 on the shaft snap passed and locate against the interior wall 30, and the operation continues as before.

The indicator cylinder may include or be replaced by an LED or other suitable electrical or electronic indicator switched by a suitable detector detecting when the device is cocked and containing a lancet. The indicator could be associated with the shaft or located elsewhere within or on the housing.

The invention claimed is:

1. A lancing device, comprising:
an outer housing (10, 11), said outer housing (10, 11) having a forward portion (14) hingeable with respect to a remainder thereof between an open position in which there is access to a lancet holder (22), and a closed position ready for lancing, the hingeable forward portion (14) being latchable (46, 48) in said closed position;
a drive shaft (20) disposed in the housing for movement between a rearward and a forward position, said drive shaft having the lancet holder (22) at a forward end for receiving in use a lancet (24);
a drive spring urging (28) said drive shaft in a forward direction, a latch arrangement (30, 34) for latching said drive shaft in a rearward cocked position with the drive spring energised;
a trigger (18) for unlatching said drive shaft from its rearward position; and
a cocking/ejecting element having an externally accessible manually operable portion (62) and being arranged to be moveable in the rearward direction to cock the drive shaft, the cocking/ejecting element (66) further being operable (82) to eject a lancet from the lancet holder, and said cocking/ejecting element (66) has an unlatching element (68) disposed to unlatch said hingeable forward portion (14) when said cocking/ejecting element moved forwardly.

2. The lancing device according to claim 1, wherein said cocking/ejecting element (66) is moveable forwardly to eject a lancet (24) from said lancet holder (22).

3. The lancing device according to claim 2, wherein said latch includes an abutment (30) provided on the interior of the housing, which cooperates with a corresponding abutment (34) on the drive shaft (20), one of said abutments (30, 34) being resiliently deflectable out of engagement with the other.

4. The lancing device according to claim 1, wherein said latch includes an abutment (30) provided on an interior of the housing, which cooperates with a corresponding abutment (34) on the drive shaft (20), one of said abutments (30, 34) being resiliently deflectable out of engagement with the other.

5. The lancing device according to claim 4, wherein the abutment (34) on said shaft (20) is resiliently deflectable, and said trigger comprises an externally accessible trigger button (18) operable to engage and displace the abutment on said shaft.

6. The lancing device according to claim 5, wherein the housing (10, 11) is generally opaque in at least a rearward portion thereof, and said trigger button (18) comprises a transparent or translucent member having an internal space, and said shaft has an indicator portion (36) on its rearward end which projects into said space when said shaft (20) is in its rearward position.

7. The lancing device according to claim 1, wherein said cocking/ejecting element (66) comprises a spring support portion (79) disposed interiorly of the housing and acted upon by opposing spring means (70, 72).

8. A lancing device according to claim 1, wherein said cocking/ejecting element (66) has a cocking abutment (76) for engaging said shaft (20) and urging it rearwardly when said cocking/ejecting element (66) is moved rearwardly.

9. The lancing device according to claim 1, wherein said cocking/ejecting element (66) has an ejection finger (82) extending forwardly and operable to enter the lancet holder (22) to eject a lancet (24) when said element is moved forwardly.

10. The lancing device according to claim 1, wherein means for biasing is provided to bias the hinging movement of said forward portion (12).

11. The lancing device according to claim 1, wherein means for damping is provided to damp hinging movement of the forward portion (12).

12. The lancing device according to claim 1, wherein a bias element is provided to bias the hinging movement of said forward portion (12).

13. The lancing device according to claim 1, wherein a damping arrangement is provided to damp hinging movement of the forward portion (12).

* * * * *

UNITED STATES PATENT AND TRADEMARK OFFICE
CERTIFICATE OF CORRECTION

PATENT NO.       : 8,388,639 B2
APPLICATION NO. : 12/673634
DATED            : March 5, 2013
INVENTOR(S)      : Nicholls et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 201 days.

Signed and Sealed this
First Day of September, 2015

Michelle K. Lee
*Director of the United States Patent and Trademark Office*